(12) United States Patent
Korlipara et al.

(10) Patent No.: US 9,290,470 B2
(45) Date of Patent: Mar. 22, 2016

(54) PROCESS FOR THE PREPARATION OF KARANJA OIL-BASED EPOXY AND ACYLOXY COMPOUNDS AS LUBRICANT BASESTOCKS

(71) Applicant: Council of Scientific & Industrial Research, New Delhi (IN)

(72) Inventors: Venkata P. Korlipara, Hyderabad (IN); Sri Lakshmi K. Mallampalli, Hyderabad (IN); Saravanan Krishnasamy, Hyderabad (IN); Badari N. P. Rachapudi, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/413,847

(22) PCT Filed: Jul. 9, 2013

(86) PCT No.: PCT/IN2013/000424
§ 371 (c)(1),
(2) Date: Jan. 9, 2015

(87) PCT Pub. No.: WO2014/009972
PCT Pub. Date: Jan. 16, 2014

(65) Prior Publication Data
US 2015/0191441 A1  Jul. 9, 2015

(30) Foreign Application Priority Data
Jul. 9, 2012 (IN) .......................... 2116/DEL/2012

(51) Int. Cl.
| | | |
|---|---|---|
| *C07D 301/02* | (2006.01) |
| *C07D 301/12* | (2006.01) |
| *C07C 67/03* | (2006.01) |
| *C07D 303/16* | (2006.01) |
| *C11C 3/00* | (2006.01) |
| *C07C 67/08* | (2006.01) |
| *C07C 67/31* | (2006.01) |
| *C10M 105/40* | (2006.01) |
| *C07D 303/42* | (2006.01) |

(52) U.S. Cl.
CPC .............. *C07D 301/12* (2013.01); *C07C 67/03* (2013.01); *C07C 67/08* (2013.01); *C07C 67/31* (2013.01); *C07D 303/16* (2013.01); *C07D 303/42* (2013.01); *C10M 105/40* (2013.01); *C11C 3/00* (2013.01); *C11C 3/006* (2013.01); *C10M 2207/2895* (2013.01); *C10N 2220/022* (2013.01); *C10N 2220/023* (2013.01); *C10N 2220/024* (2013.01); *C10N 2220/032* (2013.01); *C10N 2230/06* (2013.01); *C10N 2230/10* (2013.01); *C10N 2230/12* (2013.01); *C10N 2230/24* (2013.01); *C10N 2230/66* (2013.01); *C10N 2230/74* (2013.01); *C10N 2270/00* (2013.01)

(58) Field of Classification Search
CPC .. C07D 301/12; C07D 303/42; C07D 303/16; C07C 67/03; C07C 67/31; C07C 67/08; C07C 69/587; C07C 69/675; C07C 69/67; C11C 3/00; C11C 3/006; C10M 105/40; C10M 2207/2895; C10N 2220/023; C10N 2220/024; C10N 2220/032; C10N 2270/00
USPC ........................................................ 549/518
See application file for complete search history.

(56) References Cited

U.S. PATENT DOCUMENTS

2008/0024898 A1* 1/2008 Hillis ...................... G11B 5/49
                                                            360/61

* cited by examiner

Primary Examiner — T. Victor Oh
(74) Attorney, Agent, or Firm — Baker and Hostetler LLP; Tayan B. Patel

(57) ABSTRACT

The present invention relates to preparation of epoxy karanja oil, epoxy karanja fatty acid methyl esters and their acylated derivatives. Accordingly karanja oil and karanja fatty acid methyl esters were epoxidized using performic acid method. Karanja oil and its fatty acid methyl esters were also hydroxylated to prepare their acyloxy derivatives ($C_3$, $C_4$ & $C_6$). Both the epoxy and acyloxy derivatives of karanja oil and its methyl esters were characterized by $^1H$ NMR and IR studies. The products were evaluated for acid value (A.V.), hydroxyl value (H. V.), iodine value (I. V.), viscosity, viscosity index (V.I.), pour point, flash point and copper strip corrosion and lubricant properties like oxidation stability, air release value, evaporation loss, rust prevention characteristics, hydrolytic stability, foam stability and load carrying capacity and found to be potential base stocks for hydraulic, metal working fluids and other industrial fluids.

11 Claims, No Drawings

PROCESS FOR THE PREPARATION OF KARANJA OIL-BASED EPOXY AND ACYLOXY COMPOUNDS AS LUBRICANT BASESTOCKS

RELATED APPLICATIONS

This application is the U.S. national stage of International (PCT) Patent Application No. PCT/IN2013/000424, filed Jul. 9, 2013, which claims priority to Indian Patent Application No. 2116/DEL/2012, filed Jul. 9, 2012, the entire contents of which are herein incorporated by reference.

FIELD OF INVENTION

The present invention relates to a process for the preparation of compounds of general formula 1 comprises of acyloxy compounds of general formula A and epoxy compounds of general formula B and evaluation for their physico-chemical and lubricant properties.

General formula 1

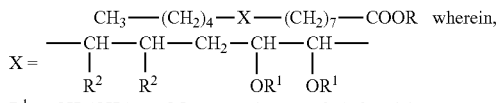

wherein, $X = $ $-CH-CH-CH_2-CH-CH-$
$\quad | \quad\;\; | \quad\quad\quad\;\; | \quad\;\; |$
$\quad R^2 \;\; R^2 \quad\quad\;\; OR^1 \;\; OR^1$ $R^1 = CH_3(CH_2)_n-CO-$ where $n = 0, 1, 2$ and $4$ $R^2 = H$ or $OCO(CH_2)n-CH_3$ where $n = 0, 1, 2$ and $4$ $R = CH_3, CH(CH_3)_2, CH_2CH(CH_3)_2, CH_2CH_2CH_2CH_3, CH_2CH(CH_2CH_3)CH_2CH_2CH_2CH_3$ or x =

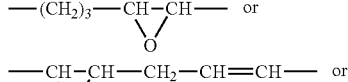  or

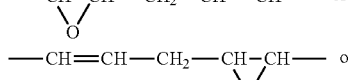  or

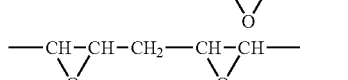  or

—CH—CH—CH₂—CH—CH—
　　\ /　　　　　\ /
　　 O　　　　　　O

General formula A

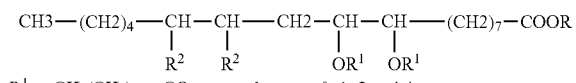

$R^1 = CH_3(CH_2)_n-CO-$ where $n = 0, 1, 2$ and $4$ $R^2 = H$ or $OCO(CH_2)n-CH_3$ where $n = 0, 1, 2$ and $4$ $R = CH_3, CH(CH_3)_2, CH_2CH(CH_3)_2, CH_2CH_2CH_2CH_3, CH_2CH(CH_2CH_3)CH_2CH_2CH_2CH_3$ General formula B

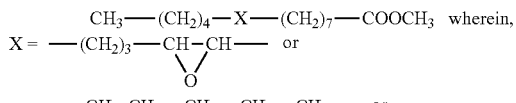 wherein, $X = $

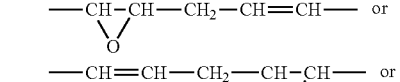 or

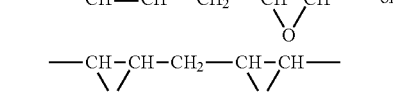 or

—CH=CH—CH₂—CH—CH— or
　　　　　　　　\ /
　　　　　　　　 O

—CH—CH—CH₂—CH—CH—
　　\ /　　　　　\ /
　　 O　　　　　　O

DESCRIPTION OF THE PRIOR ART

Vegetable oils are recognized as rapidly biodegradable and are thus promising candidates as base fluids in environment-friendly lubricants. Vegetable oils have excellent lubricity, but poor oxidation and low-temperature stability mainly due to the presence of unsaturation restricting their use as high performance lubricants. Several attempts have been made to improve their oxidation stability like transesterification with polyols like trimethylolpropane, selective hydrogenation of polyunsaturated fatty acids and conversion of unsaturation to epoxides. Among these methods to improve thermoxidative stability, epoxidation received special attention because it opens up into a wide range of reactions opening the oxirane ring. The epoxide can react with different nucleophiles to produce diols, amino alcohols, hydroxyl esters etc. was reported by Luis et at [Appl. Catal. A: Gen. 284, p. 155 (2005)]. Epoxidised soybean oil as a potential source for high temperature application lubricants was reported by Adhvaryu and Erhan et al. [Industrial Crops and Products, 15, p. 247 (2002)]. They explored the effectiveness of using epoxidized soybean oil (ESBO) in certain high temperature lubricant applications with detailed study about the thermal, oxidative and frictional behavior of ESBO. A significantly higher performance level compared with HOSBO (High oleic soya bean oil) was achieved using ESBO in certain high-temperature lubricant applications. The application of epoxidised rapeseed oil as a biodegradable lubricant is reported by Wu et al. [J. Am. Oil Chem. Soc. 77, p. 561 (2000)]. Epoxidised rape seed oil exhibited better oxidation stability, friction-reducing and extreme pressure abilities compared to rapeseed oil.

Sharmin et al., have done the preliminary studies on epoxidation, hydroxylation, acrylation and urethanation of *Linum usitatissimum* seed oil (LO) by in situ epoxidation and hydroxylation using $H_2O_2$ and acetic acid. [Eur. J. Lipid Sci. Technology, 109, p. 134, (2007)]. Harry-O'kuru et al., converted milkweed oil (*Asclepias syriaca*) in to epoxy and polyhydroxy triglycerides using in situ peroxy method. These converted products exhibit properties that can be used in many industrial applications like emulsifying properties for oil in water emulsions. [Industrial Crops and Products, 15, p. 51, (2002)].

Preparation of biodegradable lubricant basestocks with low pour points from epoxidised soybean oil by alcoholysis of the epoxy group with straight chain and iso alcohols (methyl, 1-butyl, 2-butyl, 1-hexyl, cyclohexyl, 2,2-dimethyl-1-propyl, or 1-decyl) followed by esterification of the hydroxyl groups with acid anhydrides ($C_1$, $C_4$ and $C_6$) with improved oxidation stability and low temperature characteristics was also reported. [J. Am. Oil Chem. Soc. 78, p. 1179, (2001)].

Preparation of biodegradable lubricant basestocks with low pour points from epoxidised soybean oil by alcoholysis of the epoxy group with straight chain and iso alcohols (methyl, 1-butyl, 2-butyl, 1-hexyl, cyclohexyl, 2,2-dimethyl-1-propyl, or 1-decyl) followed by esterification of the hydroxyl groups with acid anhydrides ($C_1$, $C_4$ and $C_6$) with improved oxidation stability and low temperature characteristics was also reported. [J. Am. Oil Chem. Soc. 78, p. 1179, (2001)].

Preparation of lubricant basestocks from epoxidised soybean oil, guerbet alcohols [Industrial Corps and Products, 23, p. 311 (2006)] and 2-ethyl hexyl alcohol [J. Am. Oil Chem. Soc. 80, p. 811, (2003)] was reported by Hwang et al. Adhvaryu et al., reported the preparation of bio fluids viz. soybean oil (SBO), thermally modified soybean oil (TMSBO) and chemically modified soybean oil (CMSBO) and their investigation for their potential application as industrial fluids [Wear, 257, p. 359, (2004)].

A novel process for the production of biodegradable lubricant basestocks from epoxidized vegetable oil with a lower pour point via cationic ion-exchange resins as catalysts was reported by Lathi et al., [Appl. Catal. B: Environmental, 69, p.

207, (2007)]. This involved two steps, first, ring-opening reactions by alcoholysis followed by esterification of the resultant hydroxy group in the first step.

The ring-opening reaction of epoxidized soybean oil with different alcohols such as n-butanol, iso-amyl alcohol and 2-ethylhexanol was carried out in presence of Amberlyst 15 (dry) as a catalyst. Identification of the products was confirmed by IR and NMR analysis. Pour points of the products were observed in the range of −5 to −15° C. The hydroxy group of ring-opening product of n-butanol was further reacted with acetic anhydride in presence of catalyst Amberlyst 15 (Dry) which was previously used to carry out ring-opening reaction by alcoholysis Pour point of the resulting product was observed to be −5° C. [Appl. Catal. B: Environmental, 69, p. 207, (2007)].

One pot synthesis of a novel class of chemically modified vegetable oils from epoxidised triglycerols and various anhydrides was reported by Sharma et al. The epoxy groups of the ESBO were selectively reacted with anhydrides of different chain length using a simple nucleophilic ring-opening reaction to give acyl derivatives of soybean oil using catalyst and solvent for minimum polymerization and with little disruption of the ester linkage. Hexanoic anhydride and boron trifluoride etherate catalyst were found to be the best for maximum epoxy ring opening. The resultant acyl derivatives of vegetable oil, having diester substitution at the sites of unsaturation, have potential in formulation of industrial fluids such as hydraulic fluids, lubricants and metal working fluids [Agric. Food Chem., p. 3049, (2008)].

Gast et al., reported certain new derivatives of domestically available, long chain fatty acids like ether-diesters and tri-esters of dihydroxystearic acid and pentaesters of sativic acid (9,10,12,13-tetrahydroxy stearic acid) with lower pour points [Ind. Eng. Chem., 46 (10), p. 2205, (1954)].

Nadia Salih et al., reported the synthesis of seven useful branched 2-ethylhexyl α-hydroxy stearate esters from commercially available oleic acid and common organic acids. The common organic acids used herein were octanoic, nonanoic, lauric, myristic, palmitic, stearic and behenic acids. One of the products, the behenic ester of 2-ethyl hexyl hydroxy stearate showed to have pour point, flash point and viscosity indices of −53° C., 161° C., and 215 respectively, which is favorable in the synthesis of a bio-based lubrication base fluid. [Eur. J. of Scientific Research, 31 (4), p. 583, (2009)]. These authors also reported synthesis of seven diester derivatives of 9,10, dihydroxyoctadecanoic acid by epoxidation of oleic acid. And the oxirane ring was opened with saturated aliphatic fatty acids (octanoic, nonanoic, lauric, myristic, palmitic, stearic and behenic) followed by esterification of products with butanol using $H_2SO_4$ as catalyst. The results showed that the most bulky ester groups in the mid chain with behenic acid exhibited favorable low-temperature performance [Eur. J. of Scientific Research, 31 (4), p. 273, (2009)].

Most of the studies reported in the literature so far are mainly based on edible oils, which indirectly burden the food sector. Hence, the present study aims to synthesize epoxy oil based lubricant basestocks from karanja oil which is non-edible. Karanja oil is one of the most potential feedstocks for biodiesel production in India. Development of high performance lubricant basestocks and additives from non-edible oils will have immense importance to improve the overall economics of the biodiesel process. The botanical name of karanja is *Pongamia glabra* (synonym—*P. pinnata*) and it belongs to family Leguminoseae. It is an evergreen, medium-sized glabrous tree. It reaches 15-18 meters in height, with a short bole and spreading crown. The seeds contains 27% bitter, dark colored, non-volatile oil which contains 55-60% of oleic, 13-17% of linoleic, 1.1-1.2% of gadoleic acid and around 25% of saturated fatty acids like palmitic, stearic, arachidic, behenic and lignoceric acids with an iodine value of 85 g/100 g.

Lubricant formulations using chlorinated/dehydrochlorinated and alkylated fatty acid esters of karanja oil as basestocks compounded with a commercial multifunctional additive were evaluated for their friction and wear reducing properties by optimal SRV tester and also for their load carrying properties using a four-ball tester [J. Indian Inst. Chem. Eng., 38, p. 107, (1996)]. The results are comparable with a commercial synthetic lubricant. But use of chlorinated compounds as lubricants is recently restricted due to their environment damaging effects. So, a detailed study to enhance the lubricant properties of the karanja oil like oxidative stability, low temperature and hydrolytic stability properties without effecting their biodegradability by simple chemical transformations is required. Lubricating properties of karanja oil and partially hydrogenated karanja oil without further modification were studied by Thyagarajan et al. [J. Indian Chem Soc, Ind. and News Ed., 13, p. 227, (1950), J. Indian Chem Soc, Ind. and News Ed, 13, p. 163-166, (1950)] and real efforts to modify the karanja oil or its alkyl esters to enhance their properties for their suitability as biodegradable base stocks for lubricants was not done.

Development of sulfurised karanja oil as EP additive and a formulation for industrial gear oil using the above additive was reported by Bisht et al. [J. Synthetic Lubrication, 14, p. 23, 2006]. Utilisation of sulfurised and hydrogenated karanja oil as EP additive in composition of hydraulic fluids with alkyl benzenes as basestock was demonstrated by Singh et al. These authors also reported the use of karanja oil as lubricity booster in metal working fluids [US2007060486, US2005215440], use of karanja oil and 2-ethylhexyl esters of karanja oil fatty acids as smoke inhibitor in 2-stroke gasoline engines [WO2007066348], use of karanja oil along with sodium oleate as emulsifier in metal working fluids [J. Synthetic Lubrication, 23, p. 167, (2006)]. Jain et al have used karanja oil as emulsifier in metal working lubricant formulations [J. Synthetic Lubrication, 25(3), p. 87, (2008)]. Co-sulfurisation of karanja oil with 1-tetradecene demonstrated by Churl et al. [JOTAI, 25 (4), p. 97; (1993)], appears to be a better process which gives a additive with lower pour points and higher viscosity index. By changing the relative ratios of the α-olefin and karanja oil, desired product properties for use as extreme pressure lubricant can be obtained and for applications which require high oxidative stability instead of karanja oil, its derivatives like fatty acid esters may be used for additive development.

Epoxidation of karanja oil (KO) was carried out with peroxyacetic acid that was generated in situ from aqueous hydrogen peroxide and glacial acetic acid. Unsaturated bonds in the oil were converted to oxirane by epoxidation. Almost complete epoxidation of ethylenic unsaturation was achieved. For example, the iodine value of the oil could be reduced from 89 to 19 by epoxidation at 30° C. [JAOCS, 83, p. 7 (2006)]. The same authors also demonstrated in situ epoxidation of karanja oil with aqueous hydrogen peroxide and acetic acid in the presence of amberlite IR-120 acidic ion exchange resin as catalyst. The effect of the operating variables on the oxirane oxygen content, as well as on the oxirane ring stability and the iodine value of the epoxidised karanja oil, were determined [*European Journal of Lipid Science and Technology*, 109, P. 575 (2007)]. These authors studied the epoxidation and kinetics of karanja oil and demonstrated that it is possible to develop value-added products such as epoxides from locally available natural renewable resources such as non-edible oils. The epoxy oil was not further studied for its utilization as additive or lubricant.

Patent application 0193NF2011 deals with preparation, characterization and evaluation of lubricant properties of epoxy alkyl esters of jatropha oil fatty acids and their acyloxy derivatives. Whereas, the present patent application deals with preparation, characterization and evaluation of lubricant properties of epoxy karanja oil and its epoxy methyl esters and their acyloxy derivatives. Technically they are entirely different.

From the literature it is evident that the work done based on karanja oil is mostly on preparation of additives or karanja oil as additive in various lubricant formulations. Chemical modification of karanja oil for development of lubricant basestocks received very little attention and real efforts to modify the karanja oil or its alkyl esters to enhance their properties for their suitability as biodegradable base stocks for lubricants was not done. In the present work different novel lubricant base stocks based on karanja oil and karanja fatty acid methyl esters were by their in situ epoxidation and hydroxylation followed by acylation of hydroxy groups with different acid anhydrides.

OBJECTS OF THE INVENTION

The main objective of the present invention is to provide A process for the preparation of compounds of general formula 1 comprises of acyloxy compounds of general formula A and epoxy compounds of general formula B and evaluation for their physico-chemical and lubricant properties.

General formula 1

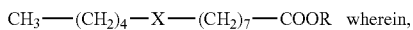
CH$_3$—(CH$_2$)$_4$—X—(CH$_2$)$_7$—COOR wherein,

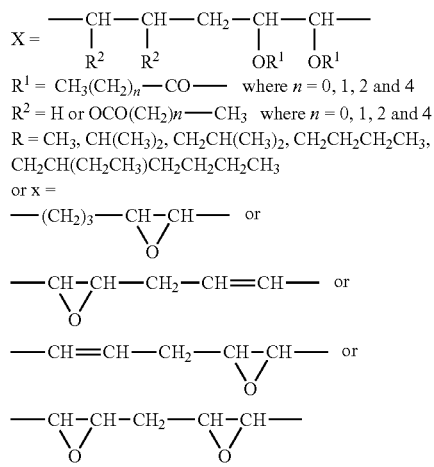

X = —CH—CH—CH$_2$—CH—CH—
　　　|　　|　　　　　|　　|
　　　R$^2$　R$^2$　　　OR$^1$　OR$^1$

R$^1$ = CH$_3$(CH$_2$)$_n$—CO— where $n$ = 0, 1, 2 and 4
R$^2$ = H or OCO(CH$_2$)$n$—CH$_3$ where $n$ = 0, 1, 2 and 4
R = CH$_3$, CH(CH$_3$)$_2$, CH$_2$CH(CH$_3$)$_2$, CH$_2$CH$_2$CH$_2$CH$_3$, CH$_2$CH(CH$_2$CH$_3$)CH$_2$CH$_2$CH$_2$CH$_3$ or x =

—(CH$_2$)$_3$—CH—CH— or
　　　　　　　\\O/

—CH—CH—CH$_2$—CH=CH— or
　　\\O/

—CH=CH—CH$_2$—CH—CH— or
　　　　　　　　　　\\O/

—CH—CH—CH$_2$—CH—CH—
　　\\O/　　　　　\\O/

General formula A

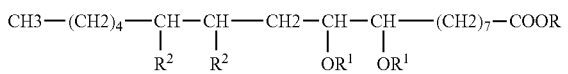
CH3—(CH2)$_4$—CH—CH—CH2—CH—CH—(CH2)$_7$—COOR
　　　　　　　|　　|　　　　　|　　|
　　　　　　　R$^2$　R$^2$　　　OR$^1$　OR$^1$

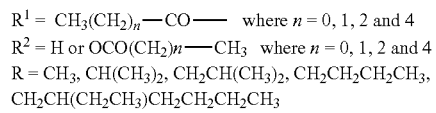

R$^1$ = CH$_3$(CH$_2$)$_n$—CO— where $n$ = 0, 1, 2 and 4
R$^2$ = H or OCO(CH$_2$)$n$—CH$_3$ where $n$ = 0, 1, 2 and 4
R = CH$_3$, CH(CH$_3$)$_2$, CH$_2$CH(CH$_3$)$_2$, CH$_2$CH$_2$CH$_2$CH$_3$, CH$_2$CH(CH$_2$CH$_3$)CH$_2$CH$_2$CH$_2$CH$_3$ General formula B

CH$_3$—(CH$_2$)$_4$—X—(CH$_2$)$_7$—COOCH$_3$ wherein,

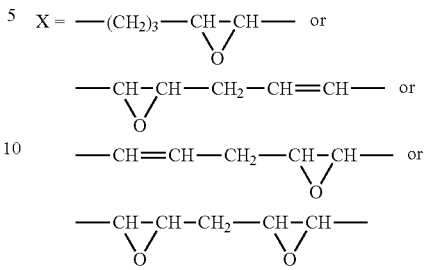

X = —(CH$_2$)$_3$—CH—CH— or
　　　　　　　　\\O/

—CH—CH—CH$_2$—CH=CH— or
　　\\O/

—CH=CH—CH$_2$—CH—CH— or
　　　　　　　　　　\\O/

—CH—CH—CH$_2$—CH—CH—
　　\\O/　　　　　\\O/

Another objective of the invention is to prepare epoxy karanja oil and epoxy karanja fatty acid methyl esters.

Another objective of the invention is to characterize the epoxy karanja oil and epoxy karanja fatty acid methyl esters for their physico-chemical and lubricant properties.

Yet another objective of the invention is to characterize acyloxy compounds of general formula 1 for their physico-chemical and lubricant properties.

SUMMARY OF THE INVENTION

The present invention provides a process for the preparation of compounds general formula 1 comprises of acyloxy compounds of general formula A and epoxy compounds of general formula B, wherein the said process comprising the steps of;

General formula 1

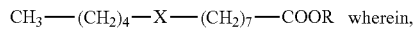
CH$_3$—(CH$_2$)$_4$—X—(CH$_2$)$_7$—COOR wherein,

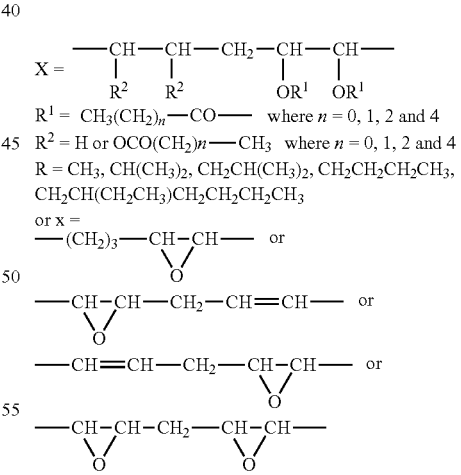

X = —CH—CH—CH$_2$—CH—CH—
　　　|　　|　　　　　|　　|
　　　R$^2$　R$^2$　　　OR$^1$　OR$^1$

R$^1$ = CH$_3$(CH$_2$)$_n$—CO— where $n$ = 0, 1, 2 and 4
R$^2$ = H or OCO(CH$_2$)$n$—CH$_3$ where $n$ = 0, 1, 2 and 4
R = CH$_3$, CH(CH$_3$)$_2$, CH$_2$CH(CH$_3$)$_2$, CH$_2$CH$_2$CH$_2$CH$_3$, CH$_2$CH(CH$_2$CH$_3$)CH$_2$CH$_2$CH$_2$CH$_3$ or x =

—(CH$_2$)$_3$—CH—CH— or
　　　　　　　\\O/

—CH—CH—CH$_2$—CH=CH— or
　　\\O/

—CH=CH—CH$_2$—CH—CH— or
　　　　　　　　　　\\O/

—CH—CH—CH$_2$—CH—CH—
　　\\O/　　　　　\\O/

General formula A

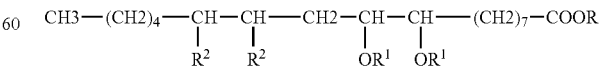
CH3—(CH2)$_4$—CH—CH—CH2—CH—CH—(CH2)$_7$—COOR
　　　　　　　|　　|　　　　　|　　|
　　　　　　　R$^2$　R$^2$　　　OR$^1$　OR$^1$

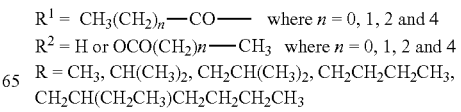

R$^1$ = CH$_3$(CH$_2$)$_n$—CO— where $n$ = 0, 1, 2 and 4
R$^2$ = H or OCO(CH$_2$)$n$—CH$_3$ where $n$ = 0, 1, 2 and 4
R = CH$_3$, CH(CH$_3$)$_2$, CH$_2$CH(CH$_3$)$_2$, CH$_2$CH$_2$CH$_2$CH$_3$, CH$_2$CH(CH$_2$CH$_3$)CH$_2$CH$_2$CH$_2$CH$_3$ General formula B

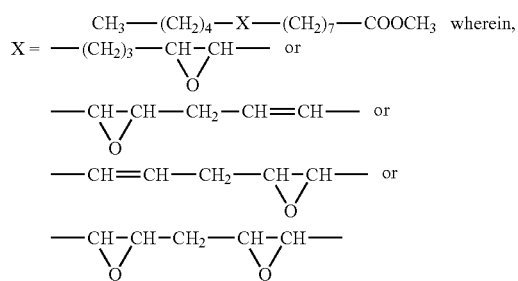

a. Stirring Karanja oil with formic acid and concentrated sulphuric acid at temperature ranging between 15-20° C. followed by addition of 30% hydrogen peroxide at 4-10° C. for a period ranging between 1 to 2 hr and then stirring the contents at 50-70° C. a period of 1-6 hr to obtain epoxy compounds of general formula. B and further stirring at 80-85° C. for a period of 6-8 hr to obtain hydroxylated oil;
b. optionally, refluxing Karanja oil with an alkali preferably, sodium hydroxide dissolved in an alcohol under stirring for a period ranging between 3-4 hrs at temperature ranging between 65-70° C. to obtain fatty acid alkyl ester further adding formic acid and concentrated sulphuric acid into it and followed by addition of 30% hydrogen peroxide at 4-15° C. for a period ranging between 1-2 hr and then stirring the contents at 50-70° C. for a period of 1-5 hr to obtain epoxy compounds of general formula B and further stirring at 80-85° C. for a period of 6-8 hr to obtain hydroxylated fatty acid alkyl ester;
c. acylating hydroxylated oil as obtained in step (a) or hydroxylated fatty acid alkyl ester as obtained in step (b) with an acid anhydrides in presence of dimethyl amino pyridine (DMAP) taken in a water azeotrope forming solvent at a temperature 140-150° C. for a period ranging between 7-9 hr to obtain acyloxy compounds of general formula A.

In one embodiment of the present invention epoxy compounds are made in the steps (a) and (b) at 15-80° C. for 0.5-10 hr and further increasing the reaction temperature to 85° C. for 5-15 hr leads to formation of hydroxylated karanja oil or hydroxylated karanja fatty acid methyl esters.

In an embodiment of the present invention no epoxy components were present in either hydroxylated karanja fatty acid methyl esters or in hydroxylated karanja oil In another embodiment of the present invention concentrated sulphuric acid used in step (a) and (b) is 2% wt of formic acid and hydrogen peroxide.

Still in another embodiment of the present invention alcohol used in step (b) is selected from the group consisting of methanol, 2-propanol, 1-butanol, 2-methyl-1-propanol and ethyl 1-hexanol.

Still in another embodiment of the present invention acid anhydrides used in step (c) is selected from the group consisting of acetic, propionic, butyric and hexanoic anhydrides.

Still in another embodiment of the present invention water azeotrope forming solvent used in step (c) is selected from the group consisting of toluene and xylene.

Still in another embodiment of the present invention yield of acyloxy compounds of general formula A is in the range of 90-95%.

Still in another embodiment of the present invention yield of epoxy compounds of general formula B is in the range of 96-98%

Still in another embodiment of the present invention acyloxy compounds of general formula A, epoxy compounds of general formula B as claimed in claim 1 are useful as lubricant basestock.

DETAILED DESCRIPTION

The present invention relates to the preparation of epoxy karanja fatty, acid methyl esters, epoxy oil, 9,10-diacyloxy octadecanoic acid and 9,10,12,13-tetraacyloxy octadecanoic acid rich-karanja fatty acid methyl esters/karanja oil as described in FIG. 1-4.

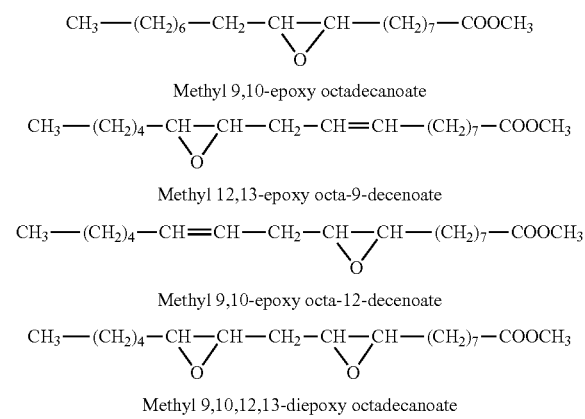

FIG. 1 Epoxy Derivatives present in Epoxidised product of Karanja Fatty Acid methyl Esters

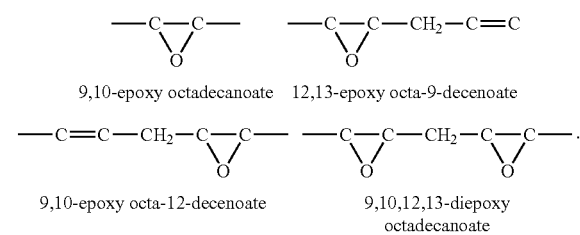

FIG. 2 Representative Epoxy Functionalities present in Epoxidised Karanja Oil

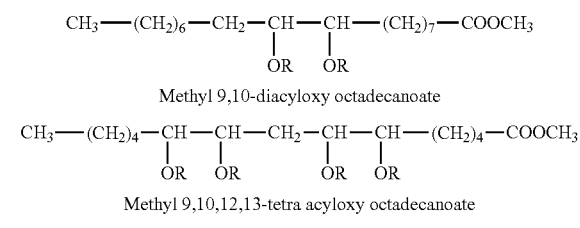

FIG. 3 Acyloxy Derivatives present in Acyloxy Product of Karanja Fatty Acid Methyl Esters

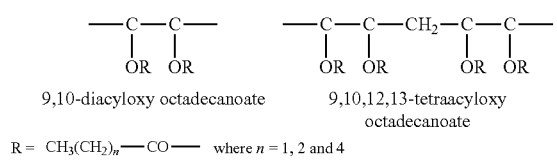

9,10-diacyloxy octadecanoate     9,10,12,13-tetraacyloxy octadecanoate

R = $CH_3(CH_2)_n$—CO—  where $n$ = 1, 2 and 4

FIG. 4 Representative Acyloxy Components present in Acyloxy Karanja Oil

The compounds epoxy fatty acid rich methyl esters, epoxy oil, 9,10-diacyloxy octadecanoic acid and 9,10,12,13-tetraacyloxy octadecanoic rich-karanja fatty acid methyl esters/oil are useful as potential lubricant basestocks for industrial fluids.

The present invention relates to a class of chemically modified karanja oil based lubricant basestocks as well as methods for producing them. In accordance with the invention, karanja fatty acid methyl esters and epoxy karanja oil were prepared starting from karanja fatty acid methyl esters and karanja oil respectively using formic acid and hydrogen peroxide in the presence of acid catalyst at 25-80° C. for 0.5-10 hr. The epoxy components present in epoxy karanja fatty acid methyl esters are methyl 9,10-epoxy octadecanoate, methyl 12,13-epoxy octa-9-decenoate, methyl 9,10-epoxy octa-12-decenoate and methyl 9,10,12,13-diepoxy octadecanoate. The epoxy components present in epoxy karanja oil are 9,10-epoxy octadecanoate, 12,13-epoxy octa-9-decenoate, 9,10-epoxy octa-12-decenoate and 9,10,12,13-diepoxy octadecanoate.

In accordance with the invention, dihydroxy and tetrahydroxy karanja oil, octadecanoic acid methyl ester rich-karanja fatty acid methyl esters were prepared by one pot synthesis from karanja oil and karanja fatty acid methyl esters using hydrogen peroxide, formic acid in presence of acidic catalyst at 25-80° C. for 0.5-10 hr for epoxidation and increasing the reaction temperature to 80-85° C. for 5-15 hr for hydroxylation. No epoxy components were present in either hydroxy karanja fatty acid methyl esters or in hydroxylated karanja oil. The hydroxylated karanja fatty acid methyl esters/oil were acylated to get 9,10-diacyloxy octadecanoic acid and 9,10,12,13-tetraacyloxy octadecanoic acid methyl ester rich-karanja fatty acid methyl esters/karanja oil.

All the karanja based epoxy products and acyloxy products were characterized for their physico-chemical and lubricant properties like hydroxyl value, total acid number, oxirane value, iodine value and evaluated for the lubricant properties like viscosity, viscosity index, pour point, flash point, copper corrosion value, rust prevention characteristics, emulsion characteristics, oxidation stability, hydrolytic stability, weld load, air release value, foam stability and noack volatility. These lubricant basestocks exhibited properties which render them useful as basestocks for biodegradable lubricant applications like hydraulic fluids, metal working fluids and other industrial fluids.

The present invention provides a process for preparation of epoxy fatty acid methyl esters, epoxy oil, 9,10-diacyloxy octadecanoic acid and 9,10,12,13-tetraacyloxy octadecanoic acid rich-karanja fatty acid methyl esters/oil of formula as described in FIG. 1-4 the steps comprising;

(a) transesterification of karanja oil with methanol using sodium hydroxide (1 wt % of substrate) as catalyst to get the corresponding karanja fatty acid methyl esters.

(b) adding formic acid and sulphuric acid to karanja oil/karanja methyl esters followed by addition of hydrogen peroxide at 0-20° C. for a period ranging between 1-3 hr and stirring the contents for a period ranging from 0.5-10 hr at 25-80° C. for epoxidation.

(c) adding formic acid and sulphuric acid to karanja oil/KFAME and followed by addition of hydrogen peroxide at 0-20° C. for a period ranging between 1 to 3 hr and then stirring the contents at 25-75° C. for a period of 2 hr and at 85-100° C. for a period of 5-15 hr for hydroxylation.

(d) acylating the 9,10-dihydroxy octadecanoic acid and 9,10,12,13-tetrahydroxy octadecanoic acid rich KFAME/oil mixture obtained in step (c) with acid anhydrides in presence of dimethyl amino pyridine (DMAP) taken in a water azeotrope forming solvent like toluene and xylene at a temperature 100-150° C. for a period required for complete conversion to obtain 9,10-di acyloxy octadecanoic acid and 9,10,12,13-tetraacyloxy octadecanoic rich KFAME/oil mixture.

The present invention provides a process wherein anhydrides used for acylation of hydroxyl groups of 9,10-dihydroxy octadecanoic acid and 9,10,12,13-tetrahydroxy octadecanoic acid were selected from a group consisting of propionic, butyric and hexanoic anhydrides in presence of DMAP in the concentration of 0.1 wt % (substrate) at 100 to 150° C.

The present invention provides a process wherein 9,10-diacyloxy octadecanoic acid and 9,10,12,13-tetraacyloxy octadecanoic rich KFAME (karanja fatty acid methyl esters)/oil mixture are useful as potential lubricant basestocks for industrial fluids.

The epoxy and acyloxy derivatives were evaluated for their physico-chemical characteristics such as acid value (A.V.), hydroxyl value (H.V.), iodine value (I.V.), oxirane value (O.V.), viscosity, viscosity index (V.I.), pour point, flash point, copper strip corrosion, oxidation stability, emulsion characteristics, foam, hydrolytic stability and weld load.

The present invention is illustrated herein below with examples, which are illustrative only and should not be construed to limit the scope of the present invention in any manner.

Example 1

Preparation of Karanja Fatty Acid Methyl Esters

Karanja oil (200 g, 0.2 mol) and sodium hydroxide (2 g, 1 wt % of substrate) dissolved in methanol (48 ml, 1.2 mol) were taken into a three neck RB flask and refluxed at 70° C. under constant mechanical stirring for 4 hr. The formation of methyl esters was monitored by TLC eluted with hexane/ethyl acetate, 90/10 (vol/vol). The weight of the product was 159.8 g (90%).

Example 2

Preparation of Epoxy Karanja Fatty Acid Methyl Esters and Evaluation of Lubricant Properties KFAME (100 g, 0.34 mol) and formic acid (19.7 ml, 0.51 mol) and sulfuric acid (1.5 ml, 2% weight of HCOOH and hydrogen peroxide) were taken into a three necked round bottomed flask and the temperature of the medium was maintained at 15° C. Hydrogen peroxide solution, 30% concentration (104.1 ml, 1.02 mol) was added slowly to the contents under mechanical stirring at 15° C. for duration of 1 hr. After addition the contents were stirred at 60° C. for 5 hr. The product was extracted hourly with ethyl acetate and washed with water until it was acid free. The obtained product was monitored by iodine value, oxirane value and gas chromatography studies. Epoxidation with an O.V 3.6 and I.V 5.4 was obtained in 1 hr. As the reaction continued, a decrease in O.V was observed. The weight of the product was 99.5 g. The formation of epoxide was confirmed by GC, GC-MS, NMR and IR spectral studies.

$^1$H NMR (CDCl$_3$, ppm): 0.88-1.0 (m, —C$\underline{H}_3$); 1.2-1.6 (m, —(C$\underline{H}_2$)$_n$—CH$_3$); 1.4-1.5 (m,

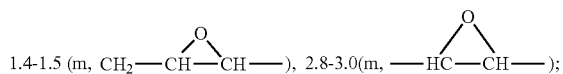

1.4-1.5 (m, CH$_2$—CH—CH—), 2.8-3.0(m, —HC—CH—);

IR (neat, cm$^{-1}$): 2926 (C—H), 1741 (C=O), 830 (epoxy ring), 1197 (C—C(=O)—O)

GC analysis:

TABLE 1

Fatty acid composition of epoxy karanja fatty acid methyl esters

| Fatty Acid | (wt %) |
|---|---|
| Palmitic C$_{16:0}$ | 11.5 |
| Stearic C$_{18:0}$ | 9.2 |
| Arachidic C$_{20:0}$ | 2.2 |
| Behenic C$_{22:0}$ | 6.6 |
| Lignoceric C$_{24:0}$ | 1.9 |
| C$_{18:1}$ epoxy | 52.9 |
| C$_{18:2}$ epoxy | 11.9 |
| others | 3.5 |

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, and weld load and the data is provided in the following table.

TABLE 2

Physico-chemical and lubricant properties of epoxy karanja fatty acid methyl esters

| Property | Value |
|---|---|
| Density 30° C. (g/cm$^3$) | 0.90602 |
| Viscosity, 40° C. cSt | 10.9 |
| 100° C. | 3.0 |
| Viscosity Index | 142 |
| Pour Point (° C.) | 15 |
| Copper strip corrosion | 1a |
| Flash point (° C.) | 192 |
| Noack evaporation loss (%) | 39.2 |
| RBOT (min) | >5 |
| Air release value (min) | 1.7 |
| Emulsion characteristics | 43-37-0 (40 min) |
| Weld load (Kg) | 190 |
| Hydrolytic Stability | |
| Cu strip weight loss | 0.0251 |
| Cu strip appearance | 1c |
| Water acidity | 169.3 |

Example 3

Preparation of Hydroxy Karanja Fatty Acid Methyl Esters

Karanja fatty acid methyl esters (100 g, 0.34 mol), formic acid (19.7 ml, 0.51 mol) and concentrated sulphuric acid (1.5 ml, 2% weight of formic acid and hydrogen peroxide) were taken into a three necked round bottomed flask and the temperature of the medium was maintained at 15° C. Hydrogen peroxide solution, 30% concentration (104.1 ml, 1.02 mol) was added slowly to the contents under mechanical stirring at 15° C. for a duration of 1 hr. After addition the contents were stirred at 60° C. for 1 hr and at 85° C. for 6 hr. The final product was extracted with ethyl acetate and washed with water until it was acid free. The weight of the product was 101.8 g. The reaction was monitored hourly by oxirane value, hydroxyl value, IR and gas chromatography studies. Hydroxylation with an H.V 155 was obtained in 7 hr. As the reaction continued, a constant HV was observed until 15 hr. The formation of hydroxyl product was confirmed by $^1$H NMR, IR and by GC and GC-MS studies after acylation of the hydroxyl product.

$^1$H NMR (CDCl$_3$, ppm): 0.88 (t, —C$\underline{H}_3$); 1.2-1.6 (m, —(C$\underline{H}_2$)$_n$—CH$_3$); 1.5-1.6 (m, —C$\underline{H}_2$—CH$_2$—C=O); 2.1-2.2 (t, —C$\underline{H}_2$—C=O); 3.2-3.4 (m, —C$\underline{H}$—OH—); 3.7 (—O—CH$_3$)

IR (neat, cm$^{-1}$): 3445 (—OH), 2925 (C—H), 1743 (C=O), 1102 (C—C(=O)—O).

GC analysis:

TABLE 3

Fatty acid composition of hydroxy karanja fatty acid methyl esters

| Fatty Acid | (wt %) |
|---|---|
| Palmitic C$_{16:0}$ | 10.5 |
| Stearic C$_{18:0}$ | 8.4 |
| Arachidic C$_{20:0}$ | 1.9 |
| Behenic C$_{22:0}$ | 5.1 |
| Lignoceric C$_{24:0}$ | 2.1 |
| C$_{18:1}$ hydroxy | 44.9 |
| C$_{18:2}$ hydroxy | 17.9 |
| others | 10.0 |

Example 4

Preparation of Propionyloxy Karanja Fatty Acid Methyl Esters

Hydroxylated karanja fatty acid methyl esters (100.1 g, 0.3 mol), propionic anhydride (79.6 ml, 0.6 mol), DMAP (0.1 g, 0.1% DMAP based on weight of hydroxylated karanja oil) and xylene (150 ml) were taken in a three necked round bottom flask and stirred at 145° C. for a period of 9 hr. The reaction was monitored by TLC and IR. The product was distilled using short path molecular distillation to remove unreacted anhydride and acid. The crude product was purified by short path distillation under 2.1×10$^{-2}$ mm Hg at 130° C. with an acid value of 1.6. The distilled product was extracted with ethyl acetate and washed with water until it was acid free and was concentrated. The weight of the product was 112.9 g without any hydroxyl value. The product was further purified by passing through basic alumina column to obtain propionyloxy esters with an acid value less than 0.1.

$^1$H NMR (CDCl$_3$, ppm): 0.8-0.9 (t, —C$\underline{H}_3$); 1.1-1.7 (m, —(C$\underline{H}_2$)$_n$—CH$_3$); 2.1-2.4 (m, —C$\underline{H}_2$—C=O); 3.6-3.7 (s, —OC$\underline{H}_3$) 4.8-5.0 (m, —C$\underline{H}$—O—CO—R)

IR (neat, cm$^{-1}$): 2927 (C—H), 1740 (C=O), 1183 (C—C(=O)—O).

GC analysis:

TABLE 4

Fatty acid composition of propionyloxy esters of karanja fatty acid methyl esters

| Fatty Acid | (wt %) |
|---|---|
| Palmitic $C_{16:0}$ | 1.2 |
| Stearic $C_{18:0}$ | 1.8 |
| Arachidic $C_{20:0}$ | 1.2 |
| Gadoleic $C_{20:1}$ | nil |
| Behenic $C_{22:0}$ | 6.5 |
| Lignoceric $C_{24:0}$ | 1.1 |
| $C_{18:1}$ propionyloxy | 39.8 |
| $C_{18:2}$ propionyloxy | 15.5 |
| others | 16.2 |

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, weld load and foam stability and the data is provided in the following table.

TABLE 5

Physico-chemical and lubricant properties of propionyloxy esters of hydroxylated karanja fatty acid methyl esters.

| Property | Value |
|---|---|
| Density, 30° C. (g/cm³) | 0.97306 |
| Viscosity, 40° C. | 25.2 |
| cSt 100° C. | 4.8 |
| Viscosity Index | 111 |
| Pour Point (° C.) | +15 |
| Copper strip corrosion | 1a |
| Rust preventive characteristics | Pass |
| Flash point (° C.) | 234 |
| Noack evaporation loss (%) | 23.4 |
| Air release value (min) | 8.15 |
| RBOT (min) | 5 |
| Emulsion characteristics | 40-40-0 (10 min) |
| Weld load (Kg) | 180 |
| Hydrolytic Stability | |
| Cu strip weight loss | 0.0011 |
| Cu strip appearance | 1b |
| Water acidity | 11.5 |
| Foam stability (ml) | |
| SequenceI 24° C. | Nil /Nil |
| SequenceII 93° C. | Nil /Nil |
| SequenceIII 24° C. | Nil/Nil |

Example 5

Preparation of Butanoyloxy Karanja Fatty Acid Methyl Esters

Hydroxylated karanja fatty acid methyl esters (100.03 g, 0.3 mol), butyric anhydride (98.2 ml, 0.6 mol), DMAP (0.1 g, 0.1% DMAP based on weight of hydroxylated karanja oil) and xylene (150 ml) were taken in a three necked round bottom flask and stirred at 145° C. for a period of 7 hr. The reaction was monitored by TLC and IR. The product was distilled using short path distillation to remove unreacted anhydride and acid. The crude product was purified by short path distillation under $8.4 \times 10^{-2}$ mm Hg at 145° C. The distilled product was extracted with ethyl acetate and washed with water until it was acid free and was concentrated. The weight of the product was 108.3 g with a hydroxyl value of 0.7 and acid value of 4.3. The product was further purified by passing through basic alumina column to obtain butanoyloxy karanja fatty acid methyl esters with an acid value less than 0.1.

$^1$H NMR (CDCl$_3$, ppm): 0.8-1.0 (t, —C$\underline{H}_3$); 1.2-1.7 (m, —(C$\underline{H}_2$)$_n$—CH$_3$); 2.2-2.4 (m, —C$\underline{H}_2$—C═O); 3.6-3.7 (s, —OC$\underline{H}_3$) 4.8-5.0 (m, —C$\underline{H}$—O—CO—R).

IR (neat, cm$^{-1}$): 2928 (C—H), 1739 (C═O), 1176 (C—C (═O)—O).

GC analysis:

TABLE 6

Fatty acid composition of butanoyloxy esters of karanja fatty acid methyl esters

| Fatty Acid | (wt %) |
|---|---|
| Palmitic $C_{16:0}$ | 1.5 |
| Stearic $C_{18:0}$ | 2.4 |
| Arachidic $C_{20:0}$ | 1.3 |
| Behenic $C_{22:0}$ | 6.3 |
| Lignoceric $C_{24:0}$ | 2.8 |
| $C_{18:1}$ butanoyloxy | 38.4 |
| $C_{18:2}$ butanoyloxy | 25.1 |
| others | 21.7 |

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, weld load and foam stability and the data is provided in the following table.

TABLE 7

Physico-chemical and lubricant properties of butanoyloxy esters of hydroxylated karanja fatty acid methyl esters

| Property | Value |
|---|---|
| Density 30° C. (g/cm³) | 0.97236 |
| Viscosity 40° C. cSt | 25.8 |
| 100° C. cSt | 4.9 |
| Viscosity Index | 114 |
| Pour Point (° C.) | +15 |
| Copper strip corrosion | 1a |
| Rust preventive characteristics | Pass |
| Flash point (° C.) | 244 |
| Noack evaporation loss (%) | 16.6 |
| Air release value (min) | 8.58 |
| RBOT (min) | 10 |
| Emulsion characteristics | 43-37-0 (90 min) |
| Weld load (Kg) | 170 |
| Hydrolytic Stability | |
| Cu strip weight loss | 0.008 |
| Cu strip appearance | 1b |
| Water acidity | 8.9 |
| Foam stability (ml) | |
| Sequence I, 24° C. | Nil/Nil |
| Sequence II, 93° C. | Nil/Nil |
| Sequence III, 24° C. | Nil/Nil |

Example 6

Preparation of Hexanoyloxy Karanja Fatty Acid Methyl Esters

Hydroxylated karanja fatty acid methyl esters (100.13 g, 0.3 mol) hexanoic anhydride (143.18 ml, 0.6 mol), DMAP (0.1 g, 0.1% DMAP based on weight of hydroxylated karanja oil) and xylene (150 ml) were taken in a three necked round bottom flask and stirred at 145° C. for a period of 9 hr. The reaction was monitored by TLC and IR. The product was distilled using short path distillation to remove unreacted anhydride and acid. The crude product was purified by short path distillation under $2.1 \times 10^{-2}$ mm Hg at 180° C. The distilled product was extracted with ethyl acetate and washed with water until it was acid free and was concentrated. The weight of the product was 137.3 g without any hydroxyl value and acid value of 9.5. The product was further purified by passing through basic alumina column to obtain hexanoyloxy esters with an acid value less than 0.1.

$^{1}$H NMR (CDCl$_{3}$, ppm): 0.8-1.0 (t; —C$\underline{H}_{3}$); 1.2-1.8 (m, —(C$\underline{H}_{2}$)$_{n}$—CH$_{3}$); 2.2-2.4 (m, —C$\underline{H}_{2}$—C=O); 3.6 (s, —OC$\underline{H}_{3}$); 4.8-5.0 (m, —C$\underline{H}$—O—CO—R).

IR (neat, cm$^{-1}$): 2927 (C—H), 1739 (C=O), 1170 (C—C(=O)—O).

GC analysis:

TABLE 8

Fatty acid composition of hexanoyloxy esters of karanja fatty acid methyl esters

| Fatty Acid | (wt %) |
|---|---|
| Palmitic C$_{16:0}$ | 1.8 |
| Stearic C$_{18:0}$ | 2.6 |
| Arachidic C$_{20:0}$ | 1.2 |
| Behenic C$_{22:0}$ | 5.8 |
| Lignoceric C$_{24:0}$ | 2.3 |
| C$_{18:1}$ hexanoyloxy | 43.4 |
| C$_{18:2}$ hexanoyloxy | 23.3 |
| others | 18.1 |

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, weld load and foam stability and the data is provided in the following table.

TABLE 9

Physico-chemical and lubricant properties of hexanoyloxy esters of hydroxylated karanja fatty acid methyl esters

| Property | Value |
|---|---|
| Density 30° C. (g/cm$^{3}$) | 0.96424 |
| Viscosity, 40° C. | 25.8 |
| cSt 100° C. | 5.1 |
| Viscosity Index | 128 |
| Pour Point (° C.) | +15 |
| Copper strip corrosion | 1a |
| Rust preventive characteristics | Pass |
| Flash point (° C.) | 222 |
| Noack evaporation loss (%) | 13.8 |
| Air release value (min) | 8.87 |
| RBOT (min) | 10 |
| Emulsion characteristics | 43-37-0 (90 min) |
| Weld load (Kg) | 170 |
| Hydrolytic Stability | |
| Cu strip weight loss | 0.0008 |
| Cu strip appearance | 1b |
| Water acidity | 8.4 |
| Foam stability (ml) | |
| Sequence I, 24° C. | Nil/Nil |
| Sequence II, 93° C. | Nil/Nil |
| Sequence III, 24° C. | Nil/Nil |

Example 7

Preparation of Epoxy Karanja Oil and Evaluation of Lubricant Properties

Karanja oil (100 g, 0.11 mol), formic acid (8.7 ml, 0.23 mol) and concentrated sulphuric acid (1.2 ml, 2% weight of formic acid and hydrogen peroxide) were taken into a three necked round bottomed flask and the temperature of the medium was maintained at 15° C. Hydrogen peroxide solution, 30% concentration (89.8 ml, 0.88 mol) was added slowly to the contents under strong mechanical stirring at 15° C. for a duration of 1 hr. After addition the contents were stirred at 60° C. for 5 hr. The product was extracted hourly with ethyl acetate and washed with water until it was acid free. The obtained product was monitored by iodine value (IV), oxirane value (OV) and gas chromatography studies. Epoxidation with an OV 4.2 and IV 5.1 was obtained in 2 hr. As the reaction continued, a decrease in OV was observed. The weight of the product was 99.4 g. The formation of epoxide was confirmed by $^{1}$H NMR, IR and after transesterification by GC, GC-MS studies.

$^{1}$H NMR (CDCl$_{3}$, ppm): 0.88 (m, —C$\underline{H}_{3}$); 1.2-1.6 (m, —(C$\underline{H}_{2}$)$_{n}$—CH$_{3}$); 1.4-1.5 (m,

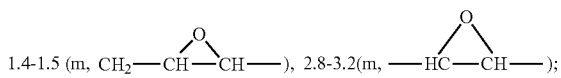

1.4-1.5 (m, CH$_{2}$—C$\overset{O}{\overset{/\ \backslash}{H}}$CH—), 2.8-3.2(m, —H$\overset{O}{\overset{/\ \backslash}{C}}$CH—);

IR (neat, cm$^{-1}$): 2926 (C—H), 1740 (C=O), 822-928 (epoxy ring), 1218-1165 (C—C(=O)—O).

GC analysis:

TABLE 10

Fatty acid composition of epoxy karanja oil

| Fatty Acid | (wt %) |
|---|---|
| Palmitic C$_{16:0}$ | 11.0 |
| Stearic C$_{18:0}$ | 8.0 |
| Arachidic C$_{20:0}$ | 1.8 |
| Behenic C$_{22:0}$ | 4.5 |
| Lignoceric C$_{24:0}$ | 1.2 |
| Epoxy C$_{18:1}$ | 53.3 |
| Epoxy C$_{18:2}$ | 12.5 |
| others | 5.5 |

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, and weld load and the data is provided in the following table.

TABLE 11

Physico-chemical and lubricant properties of epoxy karanja oil

| Property | Value |
|---|---|
| Density 30° C. (g/cm$^{3}$) | 0.98178 |
| Viscosity, 40° C. | 256.2 |
| cSt 100° C. | 27.98 |
| Viscosity Index | 144 |
| Pour Point (° C.) | 9 |
| Copper strip corrosion | 1a |
| Rust prevention characteristics | Pass |
| Flash point (° C.) | 172 |
| Noack evaporation loss (%) | 2.7 |
| RBOT (min) | 45 |

TABLE 11-continued

Physico-chemical and lubricant properties of epoxy karanja oil

| Property | Value |
|---|---|
| Air release value (min) | 17.3 |
| Weld load (Kg) | 220 |
| Foam stability (ml) | |
| Sequence I, 24° C. | Nil/Nil |
| Sequence II, 93° C. | Nil/Nil |
| Sequence III, 24° C. | Nil/Nil |

Example 8

Preparation of Hydroxy Karanja Oil

Karanja oil (100 g, 0.11 mol), formic acid (8.7 ml, 0.23 mol) and concentrated sulphuric acid (1.2 ml, 2% weight of formic acid and hydrogen peroxide) were taken into a three necked round bottomed flask and the temperature of the medium was maintained at 15° C. Hydrogen peroxide solution, 30% concentration (89.8 ml, 0.88 mol) was added slowly to the contents under mechanical stirring at 15° C. for a duration of 1 hr. After addition the contents were stirred at 60° C. for 2 hr and at 85° C. for 7 hr. The final product was extracted with ethyl acetate and washed with water until it was acid free. The weight of the product was 102.2 g. The reaction was monitored hourly by oxirane value (OV), hydroxyl value (HV), IR and gas chromatography studies. Hydroxylation with an HV 167 was obtained in 7 hr. As the reaction continued, a constant HV was observed until 15 hr. The formation of hydroxyl product was confirmed by $^1$H NMR, IR and after acylation of the hydroxyl product by GC and GC-MS studies.

$^1$H NMR (CDCl$_3$, ppm): 0.8-1.0 (t, —C$\underline{H}_3$); 1.2-1.6 (m, —(C$\underline{H}_2$)$_n$—CH$_3$); 1.5-1.6 (m, —C$\underline{H}_2$—CH$_2$—C=O); 2.1-2.2 (t, —C$\underline{H}_2$—C=O); 3.2-3.4 (m, —C$\underline{H}$—OH—); 4.0-4.4 (m, sn-1, sn-3); 5.2 (m, sn-2)

IR (neat, cm$^{-1}$): 3445 (—OH), 2925 (C—H), 1743 (C=O), 1102 (C—C(=O)—O).

GC analysis:

TABLE 12

Fatty acid composition of hydroxy karanja oil

| Fatty Acid | (wt %) |
|---|---|
| Palmitic C$_{16:0}$ | 11.5 |
| Stearic C$_{18:0}$ | 9.2 |
| Arachidic C$_{20:0}$ | 2.2 |
| Behenic C$_{22:0}$ | 5.7 |
| Lignoceric C$_{24:0}$ | 2.5 |
| C$_{18:1}$ hydroxy | 42 |
| C$_{18:2}$ hydroxy | 10.6 |
| others | 14.1 |

Example 9

Preparation of Propionyloxy Karanja Oil

Hydroxylated karanja oil (100.13 g, 0.09 mol) propionic anhydride (33.4 ml, 0.3 mol), DMAP (0.1% DMAP based on weight of hydroxylated karanja oil) and xylene (150 ml) were taken in a three necked round bottom flask and stirred at 145° C. for a period of 7 hr. The reaction was monitored by TLC and IR. The product was distilled using short path molecular distillation unit to remove unreacted anhydride and acid. The crude product was purified by short path distillation under 2.1×10$^{-2}$ mm Hg at 160° C. The distilled product was extracted with ethyl acetate and washed with water until it was acid free and was concentrated. The weight of the product was 109.1 g with a hydroxyl value of 7.95 and acid value of 6.3. The product was further purified by passing through basic alumina column to obtain propionyloxy karanja oil with an acid value less than 0.1.

$^1$H NMR (CDCl$_3$, ppm): 0.8 (t, —C$\underline{H}_3$); 1.2-1.6 (m, —(C$\underline{H}_2$)$_n$—CH$_3$); 2.2-2.4 (t, —C$\underline{H}_2$—C=O); 4.0-4.4 (m, sn-1, sn-3); 5.2 (m, sn-2); 4.8-5.4 (m, —C$\underline{H}$—O—CO—R).

IR (neat, cm$^{-1}$): 2926 (C—H), 1742 (C=O), 1178 (C—C(=O)—O).

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, weld load and foam stability and the data is provided in the following table.

TABLE 13

Physico-chemical and lubricant properties of propionyloxy esters of hydroxylated karanja oil

| Property | Value |
|---|---|
| Viscosity at 100° C. cSt | 63.7 |
| Pour Point (° C.) | 12 |
| Copper strip corrosion | 1a |
| Rust prevention characteristics | Pass |
| Flash point (° C.) | 228 |
| Noack evaporation loss (%) | 4.2 |
| RBOT (min) | 10 |
| Air release value (min) | 43.7 |
| Weld load (Kg) | 210 |
| Hydrolytic Stability | |
| Cu strip weight loss | 0.0012 |
| Cu strip appearance | 1a |
| Water acidity | 5.16 |
| Foam stability (ml) | |
| Sequence I, 24° C. | Nil/Nil |
| Sequence II, 93° C. | Nil/Nil |
| Sequence III, 24° C. | Nil/Nil |

Example 10

Preparation of Butanoyloxy Karanja Oil

Hydroxylated karanja oil (100.13 g, 0.09 mol), butyric anhydride (46.9 ml, 0.29 mol), DMAP (0.1% DMAP based on weight of hydroxylated karanja oil) and xylene (150 ml) were taken in a three necked round bottom flask and stirred at 145° C. for a period of 7 hr. The reaction was monitored by TLC and IR. The product was distilled using short path distillation to remove unreacted anhydride and acid. The crude product was purified by short path distillation under 2.1×10$^{-2}$ mm Hg at 180° C. The distilled product was extracted with ethyl acetate and washed with water until it was acid free and was concentrated. The weight of the product was 116.1 g with a hydroxyl value of 0.09 and acid value of 4.3. The product was further purified by passing through basic alumina column to obtain butanoyloxy karanja oil with an acid value less than 0.1.

$^1$H NMR (CDCl$_3$, ppm): 0.8 (t, —C$\underline{H}_3$); 1.2-1.6 (m, —(C$\underline{H}_2$)$_n$—CH$_3$); 2.2-2.4 (m, —C$\underline{H}_2$—C=O); 4.0-4.4 (m, sn-1, sn-3); 5.2 (m, sn-2); 4.8-5.4 (m, —C$\underline{H}$—O—CO—R).

IR (neat, cm$^{-1}$): 2928 (C—H), 1738 (C=O), 1176 (C—C (=O)—O).

The product was evaluated for lubricant properties, i.e. density, viscosity, viscosity index (V.I), pour point, flash point, Cu strip corrosion, air release value, rust prevention characteristics, oxidation stability (RBOT), hydrolytic stability, weld load and foam stability and the data is provided in the following table.

TABLE 14

Physico-chemical and lubricant properties of butanoyloxy esters of hydroxylated karanja oil

| Property | Value |
| --- | --- |
| Viscosity at 100° C. cSt | 145.6 |
| Pour Point (° C.) | 9 |
| Copper strip corrosion | 1a |
| Rust prevention characteristics | Pass |
| Flash point (° C.) | >275 |
| Noack evaporation loss (%) | 3.2 |
| RBOT (min) | 10 |
| Air release value (min) | 42.8 |
| Weld load (Kg) | 210 |
| Hydrolytic Stability | |
| Cu strip weight loss | 0.0017 |
| Cu strip appearance | 3b |
| Water acidity | — |
| Foam stability (ml) | |
| Sequence I, 24° C. | Nil/Nil |
| Sequence II, 93° C. | 20/Nil |
| Sequence III, 24° C. | Nil/Nil |

Example 11

Preparation of Hexanoyloxy Karanja Oil

Hydroxylated karanja oil (100.13 g, 0.09 mol) hexanoic anhydride (63.6 ml, 0.29 mol), DMAP (0.1 g, 0.1% DMAP based on weight of hydroxylated karanja oil) and xylene (150 ml) were taken in a three necked round bottom flask and stirred at 145° C. for a period of 9 hr. The reaction was monitored by TLC and IR. The product was distilled using short path molecular distillation to remove unreacted anhydride and acid. The crude product was purified by short path distillation under $4.9 \times 10^{-2}$ mm Hg at 200° C. The distilled product was extracted with ethyl acetate and washed with water until it was acid free and was concentrated. The weight of the product was 117.1 g with a hydroxyl value of 10.05 and acid value of 2.6. The product was further purified by passing through basic alumina column to obtain hexanoyloxy karanja oil with an acid value less than 0.1.

$^1$H NMR (CDCl$_3$, ppm): 0.8 (t, —CH$_3$); 1.2-1.6 (m, —(CH$_2$)$_n$—CH$_3$); 2.2-2.4 (t, —CH$_2$—C=O); 4.0-4.4 (m, sn-1, sn-3); 5.2 (m, sn-2); 4.8-5.4 (m, —CH—O—CO—R).

IR (neat, cm$^{-1}$): 2928 (C—H), 1740 (C=O), 1169 (C—C (=O)—O).

The product was evaluated for lubricant properties, i.e. density, viscosity, viscosity index (V.I), pour point, flash point, Cu strip corrosion, air release value, rust prevention, emulsion characteristics, oxidation stability, hydrolytic stability, weld load and foam stability and the data is provided in the following table.

TABLE 15

Physico-chemical and lubricant properties of hexanoyloxy esters of hydroxylated karanja oil

| Property | Value |
| --- | --- |
| Viscosity at 100° C., cSt | 36.5 |
| Pour Point (° C.) | 9 |
| Copper strip corrosion | 1a |
| Rust prevention characteristics | Pass |
| Flash point (° C.) | 288 |
| Noack evaporation loss (%) | 3.1 |
| RBOT (min) | 12 |
| Air release value (min) | 26.9 |
| Weld load (Kg) | 200 |
| Hydrolytic Stability | |
| Cu strip weight loss | 0.0009 |
| Cu strip appearance | 1b |
| Water acidity | 12.6 |
| Foam stability (ml) | |
| Sequence I, 24° C. | 10/Nil |
| Sequence II, 93° C. | 20/Nil |
| Sequence III, 24° C. | Nil/Nil |

Advantages of the Present Invention

The search for environmentally friendly materials that have the potential to substitute for mineral oil in various industrial applications is currently being considered a top priority in the fuel and energy sector. Renewable resources such as seed oils and their derivatives are being considered as potential replacements for mineral oil based raw materials in certain industrial applications where immediate contact with the environment is anticipated. Chemically modified vegetable oil based lubricants are not only made from renewable resources but also possess better biodegradability. Hence vegetable oil based lubricants have a lot of importance in the coming years as possible substitutes for petroleum based lubricants. As very few groups are working in the area of biolubricants CSIR can build a good portfolio in this new area. The present invention describes the preparation of Karanja oil based epoxy and acyloxy based derivatives. As these compounds exhibited good lubricant properties, they can be commercially exploited as lubricant base stocks.

What is claimed is:

1. A process for the preparation of compounds of formula 1 comprising acyloxy compounds of formula A and epoxy compounds of formula B, wherein the process comprises the steps of:

formula 1

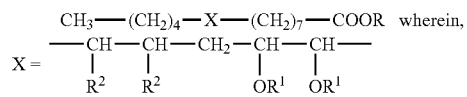
wherein,
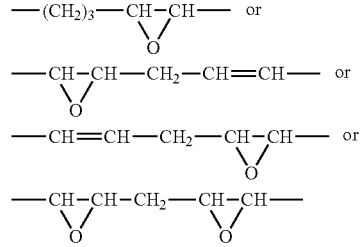
$R^1 = CH_3(CH_2)_n$—CO— where $n = 0, 1, 2$ and $4$
$R^2 = $ H or $OCO(CH_2)n$—$CH_3$ where $n = 0, 1, 2$ and $4$
$R = CH_3, CH(CH_3)_2, CH_2CH(CH_3)_2, CH_2CH_2CH_2CH_3,$
$CH_2CH(CH_2CH_3)CH_2CH_2CH_2CH_3$
or x =
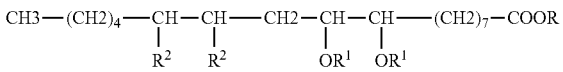

formula A $CH_3—(CH_2)_4—CH—CH——CH_2—CH—CH——(CH_2)_7—COOR$
with $R^2, R^2, OR^1, OR^1$ substituents
$R^1 = CH_3(CH_2)_n$—CO— where $n = 0, 1, 2$ and $4$
$R^2 = $ H or $OCO(CH_2)n$—$CH_3$ where $n = 0, 1, 2$ and $4$
$R = CH_3, CH(CH_3)_2, CH_2CH(CH_3)_2, CH_2CH_2CH_2CH_3,$
$CH_2CH(CH_2CH_3)CH_2CH_2CH_2CH_3$ formula B

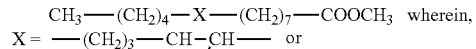 wherein,
X = 
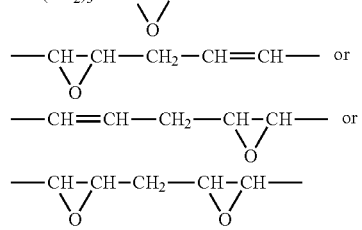

a. Stirring Karanja oil with formic acid and concentrated sulphuric acid at a temperature ranging between 15-20° C. followed by the addition of 30% hydrogen peroxide at 4-10° C. for a period ranging between 1 to 2 hrs, and then stirring the contents at 50-70° C. for a period of 1-6 hrs to obtain epoxy compounds of the formula B and further stirring at 80-85° C. for a period of 6-8 hrs to obtain hydroxylated oil;

b. optionally, refluxing Karanja oil with an alkali dissolved in an alcohol under stirring for a period ranging between 3-4 hrs at a temperature ranging between 65-70° C. to obtain fatty acid alkyl ester, and further adding formic acid and concentrated sulphuric acid into it, followed by the addition of 30% hydrogen peroxide at 4-15° C. for a period ranging between 1-2 hrs and then stirring the contents at 50-70° C. for a period of 1-5 hrs to obtain epoxy compounds of the formula B and further stirring at 80-85° C. for a period of 6-8 hrs to obtain hydroxylated fatty acid alkyl ester;

c. acylating the hydroxylated oil as obtained in step (a) or the hydroxylated fatty acid alkyl ester as obtained in step (b) with acid anhydrides in the presence of dimethyl amino pyridine (DMAP) taken in a water azeotrope forming solvent at a temperature of 140-150° C. for a period ranging between 7-9 hrs to obtain the acyloxy compounds of formula A.

2. A process as claimed in claim 1, wherein epoxy compounds are made in steps (a) and (b) at 25-80° C. for 0.5-10 hrs, and further increasing the reaction temperature to 80-85° C. for 5-15 hrs which leads to formation of hydroxylated Karanja oil or hydroxylated Karanja fatty acid methyl esters.

3. A process as claimed in claim 2, wherein no epoxy components are present either in the hydroxylated Karanja fatty acid methyl esters or in the hydroxylated karanja oil.

4. A process as claimed in claim 1, wherein the concentrated sulphuric acid used in steps (a) and (b) is 2 wt % of formic acid and hydrogen peroxide.

5. A process as claimed in claim 1, wherein the alcohol used in step (b) is selected from the group consisting of methanol, 2-propanol, 1-butanol, 2-methyl-1-propanol and ethyl 1-hexanol.

6. A process as claimed in claim 1, wherein the acid anhydrides used in step (c) are selected from the group consisting of acetic, propionic, butyric and hexanoic anhydrides.

7. A process as claimed in claim 1, wherein the water azeotrope forming solvent used step (c) is selected from the group consisting of toluene and xylene.

8. A process as claimed in claim 1, wherein yield of the acyloxy compounds of formula A is in the range of 90-95%.

9. A process as claimed in claim 1, wherein yield of the epoxy compounds of formula B is in the range of 96-98%.

10. A process as claimed in claim 1, wherein the acyloxy compounds of formula A and the epoxy compounds of formula B are useful as lubricant basestock.

11. A process as claimed in claim 1, wherein the alkali in step (b) includes sodium hydroxide.

* * * * *